United States Patent [19]

Nakagawa et al.

[11] Patent Number: 4,526,570
[45] Date of Patent: Jul. 2, 1985

[54] DENTAL HYGIENIC DEVICE

[75] Inventors: Yoshinori Nakagawa, Nara; Tsutomu Yoneda, Kishiwada; Shoji Matsuda, Osaka, all of Japan

[73] Assignee: Shiken, Ltd., Osaka, Japan

[21] Appl. No.: 436,436

[22] Filed: Oct. 25, 1982

[51] Int. Cl.³ .................. A46B 15/00; A61N 1/30
[52] U.S. Cl. ........................................... 604/20
[58] Field of Search ................ 604/20; 128/393, 67; 136/291

[56] References Cited

U.S. PATENT DOCUMENTS

| | | | |
|---|---|---|---|
| 2,834,344 | 5/1958 | Kanai | 604/20 |
| 3,412,731 | 11/1968 | Reynolds | 604/20 |
| 3,478,741 | 11/1969 | Simor | 604/20 |
| 3,520,297 | 7/1970 | Bechtold | 604/20 |
| 3,716,054 | 2/1973 | Porter et al. | 604/20 |
| 3,831,598 | 8/1974 | Tice | 604/20 |
| 4,149,533 | 4/1979 | Ishikawa et al. | 604/20 |

FOREIGN PATENT DOCUMENTS

| | | | |
|---|---|---|---|
| 1059749 | 3/1954 | France | 604/20 |
| 158249 | 5/1982 | Japan . | |
| 156184 | 5/1982 | Japan . | |
| 138018 | 3/1983 | Japan . | |
| 406137 | 8/1966 | Switzerland | 604/20 |

OTHER PUBLICATIONS

*Playboy Magazine*, advertisement 2/1983 "Solar-Powered Vibrator".
"Uses of Solar Energy", Amperex.
"Energizing Watch Cells with Sunlight", Jewelers' Circular-*Keystone*, Mar. 1977, reprinted by Solarex Corporation, (Maryland).
"Nature", Fujshima, et al., Electrochemical Photolysis of Water at a Semiconductor Electrode, vol. 238, pp.37-38, (1972).
"Photocatalysis" by David F. Ollis.

*Primary Examiner*—C. Fred Rosenbaum
*Assistant Examiner*—Michelle N. Lester
*Attorney, Agent, or Firm*—Cushman, Darby & Cushman

[57] ABSTRACT

A dental hygienic device comprising an n-type semiconductor disposed on or in a main body consisting of an inserting portion and a handle. At least one portion of the semiconductor is exposed while at least the other portion being located at the inserting portion of said main body. The semiconductor, when irradiated with a natural and/or man-made light, is activated to produce therein a number of holes whereas teeth becomes reverse-phased due to an electron density higher than that in the semiconductor to thereby give rise to a reduction which decompose tartars and colored scales on the teeth.

10 Claims, 9 Drawing Figures

DENTAL HYGIENIC DEVICE

BACKGROUND OF THE INVENTION

1. Field of the Invention

The present invention relates to a dental hygienic device having a structure based on and utilizing a photoelectric chemical reaction, and more particularly to a dental hygienic device adapted to improve sanitary conditions of teeth by means of an electrical polarization and chemical reduction which are produced by electrical energy that is converted from photoenergy by a semiconductor under coexistence of a light beam, water and the user's teeth.

2. Description of the Prior Art

Tooth powders or pastes contain an adequate amount of fluorine compounds because such flourine compounds have proved to be effective for promoting healthy teeth.

Teeth surfaces however tend to prevent anions, such as fluorine, from permeating the teeth since the teeth are covered with saliva which have a pH value lower than the pH value of the teeth. It has been, therefore, very difficult to obtain satisfactory effects from e.g. fluorine.

In some proposals for solving such a problem, a cathode is attached to a brushing head of a toothbrush. In use of such a device, the teeth-ridges or teeth per se will act as a cathode while the human body will function as a conductor whereby under presence of saliva and/or drinking water an electrolytic reaction takes place as follows:

$$H_2O \rightarrow \tfrac{1}{2}O_2 + 2H^+ + 2e^- \ldots \text{(anode reaction),}$$

$$2H^+ + 2e^- \rightarrow H_2 \ldots \text{(cathode reaction)}$$

and as the result, $$H_2O \rightarrow \tfrac{1}{2}O_2 + H_2.$$

The above reaction improves the permeability of fluorine ions.

This technique is however not convenient in that is needs a comparatively large consumption of electric power for such reactions since the human body (the electric resistance of which is high) is used as a circuit component. Its further disadvantage resides in the fact that there is a considerable difference between individuals in view of electric resistance to such a degree that the required current strength for such reactions might not be achieved. Moreover, misapplication of a high voltage which would overcome the problem could cause injury to the user's body. Hence, a novel technology has been sought which would not have the above-discussed disadvantages of electrolysis notwithstanding the utilization of electric energy.

SUMMARY OF THE INVENTION

It is an object of the present invention to provide a dental hygienic device effectively adapted to solve the problems in the prior art to decompose and remove tartar and colored scale from teeth in order to protect them from decay of dentin or from internal purulency of gums closely holding the teeth. The device of the present invention is also effective to prevent socalled "ash-extraction" caused by a lower pH value of teeth.

The dental hygienic device comprises, according to the present invention, a fundamental member or main body provided with an insertion portion to be inserted into an oral cavity, and an n-type semiconductor member having a photoelectric effect and disposed on or in the main body so as to be partially exposed while also partially being located at the insertion portion of the main body.

An important difference between the prior art and the present invention resides in the fact that the former utilizes electrolytic reactions whereas the latter makes use of the socalled photoelectric chemical reaction which includes or gives rise to reactions generally occurring in electric cells, i.e. oxidation and reduction.

In accordance with the present invention, an n-type semiconductor material (preferably $TiO_2$) is provided and when brought into operative association with saliva and/or water in an oral cavity will effect an oxidation reaction to occur at the semiconductor while a reduction reaction occurs at the teeth. The phenomenon of electrochemical photolysis of water using n-type semiconductor material is generally known. In this regard, see Fujishima, et al., "Electrochemical Photolysis of Water at a Semiconductor Electrode", Nature, Vol. 238, pp. 37-38 (1972). The present invention in a broad sense utilizes this phenomonon in a dental hygienic device so as to promote hygienic care for a user's teeth.

As used herein the terms oxidation and reduction do not merely mean bonding of oxygen with or dissociation thereof from a certain substance that is observed, for example, in combustion, corrosion or any other chemical reactions, but is intended to refer to electrons being taken from or given to any concerred substance. This concept has, as well known, originated from an electrical understanding of the ionic bonds, especially of the oxidation and reduction involved in chemical reactions.

The characteristics of the invention will be explained below in greater detail.

The n-type semiconductor member having a photoelectric effect is inserted into and withdrawn from an oral cavity when teeth are brushed. The semiconductor will be electrically excited when it is irradiated with natural light and, at the same time, will be given a number of holes caused by an electric potential difference between it and an electrostatic layer formed in the air in contact with the semiconductor. The electric holes polarize the teeth making the semiconductor material an anode. Such a phenomenon is an intrinsic function of such semiconductors as indicated above.

On the other hand, the teeth will become reverse-phased in polarity due to their electron density being different from (i.e. higher than) that of said semiconductor. Namely, the teeth become a cathode. Therefore, saliva or water near the semi-conductor within the oral cavity will give up electrons to the holes of the semiconductor thereby oxidizing the saliva or water. A reduction reaction simultaneously takes place at the teeth or the tartar deposited thereon while they are obtaining electrons from the saliva or water.

It is to be emphasized that the reactions occuring in electric cells as well as the oxidation and reduction will take place at the same time, the former being observed between the semiconductor functioning as the anode and the teeth functioning as the cathode. The latter are observed with the photo-irradiated semiconductor as accepting electrons from the saliva or water near the semiconductor, and with the teeth and tartar accepting electrons from the semiconductor. Consequently, the above reduction will thus neutralize the teeth whose pH value has been lowered by the tartar and scale so that ash-extraction due to the low pH can be remarkably avoided.

The aforemented polarization will decompose the colored scale and the tartar causing the decay. Thus, gum purulency as well as decay are efficiently prevented while the teeth are maintained in a more beautiful state.

Other objects and merits of the invention will become apparent in the course of following description with reference to the accompanying drawings showing preferred embodiments of the invention.

DETAILED DESCRIPTION OF PREFERRED EMBODIMENTS

Figure 1:
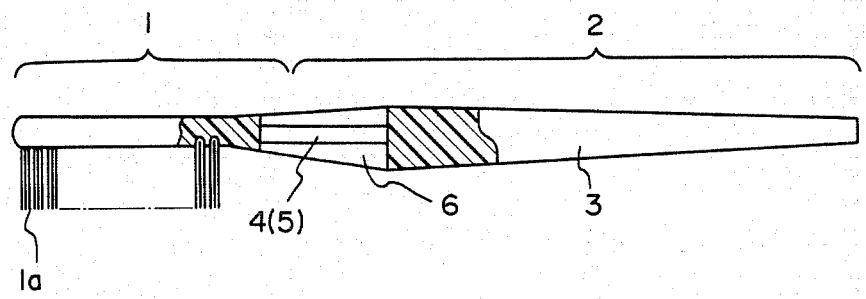
FIG. 1 is a front elevation of a dental hygienic device in an embodiment of this invention, with a surface portion partially removed.
Figure 2:
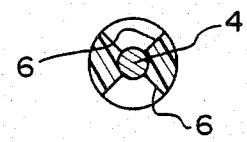
FIG. 2 is a vertical section of the device in FIG. 1.

FIGS. 1 and 2 illustrate the dental hygienic device of the present invention that is embodied in a toothbrush by attaching thereto a semiconductor member preferably of n-type having a photoelectric effect which will be referred to hereinafter. A fundamental member or main body 3 is constructed of a suitable plastic and comprises an inserting portion 1 and a handle 2, the portion 1 having in a known manner a brush 1a upstanding therefrom and adpated for insertion into an oral cavity (not shown). The handle 2 is positioned exteriorly of the cavity in use of the device. A semiconductor 4 which is preferrably wire-shaped (having a diameter of about 3 mm) or alternatively ribbon-shaped is embedded in the main body 3 so as to extend from the inserting portion 1 to the handle 2. In such structure as just described above, the semiconductor per se functions as a conductive material for photoelectrons. Grooves 6 formed in the main body 3 are utilized for embedding the semiconductor during the manufacture of the device while on the other hand acting as a means to pool water and/or saliva during use thereof. The body 3, when made from a transparent material, may almost entirely embed the semiconductor 4 with an internal end thereof exposed such that it contacts saliva or water in the oral cavity.

Figure 3:
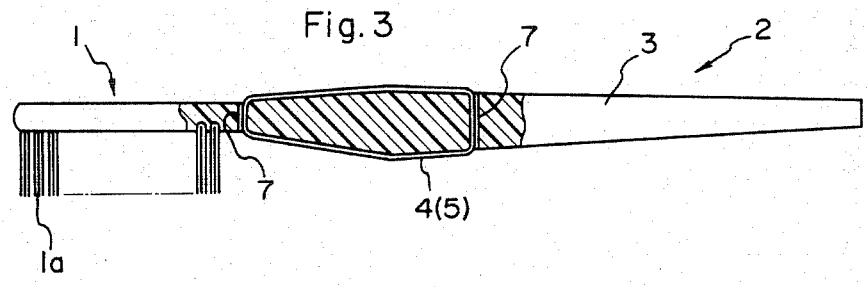
FIGS. 3 to 6 respectively show other embodiments each illustrated with a portion removed similarly to FIG. 1.

In another embodiment shown in FIG. 3, one or two pieces of semiconductors 4 extend through apertures 7, 7 to thereby form a closed loop exposed on the front and/or backside of the main body 3. Other structures are similar to those in FIG. 1 so that the same indicating numerals are given to them without any further description thereof as is also the case with the other embodiments described below.

Figure 4:
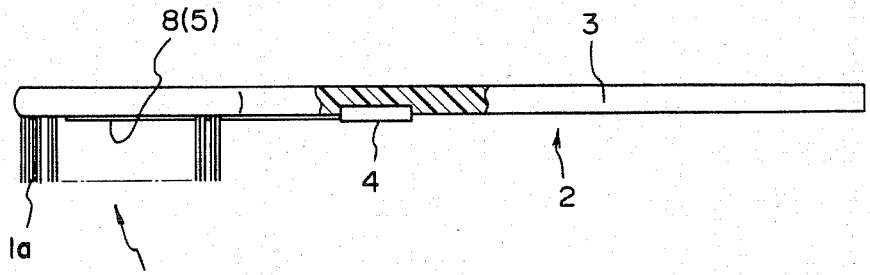

In a still further embodiment illustrated in FIG. 4, a small-sized semiconductor 4 is secured to a handle 2. A conductive wire 8 extends from the semiconductor to an inserting portion 1 thereby to conduct photoelectrons.

Figure 5:
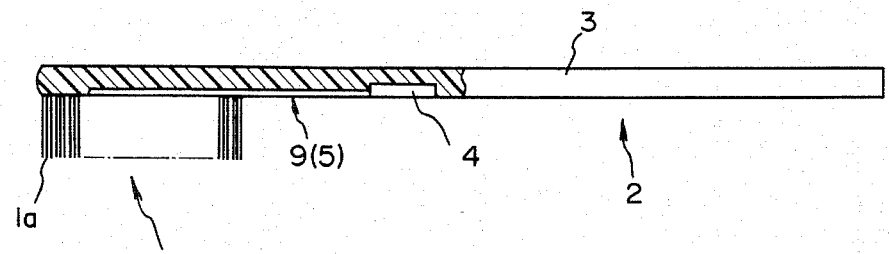

A groove 9 is formed on a main body 3 in a further embodiment in FIG. 5, so as to hold an amount of water or saliva therein which acts as a conductive line for photoelectrons instead of the wire 8.

Figure 6:
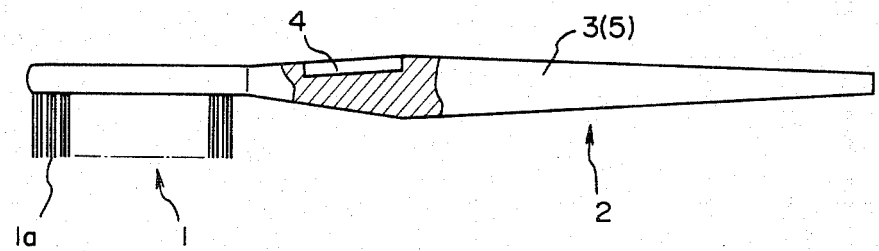

In a still further embodiment shown in FIG. 6, a main body 3 is of a conductive material (which should be harmless to human bodies).

An example of preferable semiconductors 4 is titanium dioxide ($TiO_2$) which may be produced by intensely heating elemental titanium (Ti) at 1200° to 1500° C. in an incandescent state for 2 to 5 minutes. It is of course possible, however, to make use of any other kind of semiconductors which may give rise to a photoelectric current of a suitable intensity when exposed to natural light and may include some semiconductors that are treated with pigments or complex compounds to increase their quantum coefficiency. As for the shapes or states of the semiconductors, they may be plates, wires, ribbons or sintered or coalescent powders.

Figure 7:
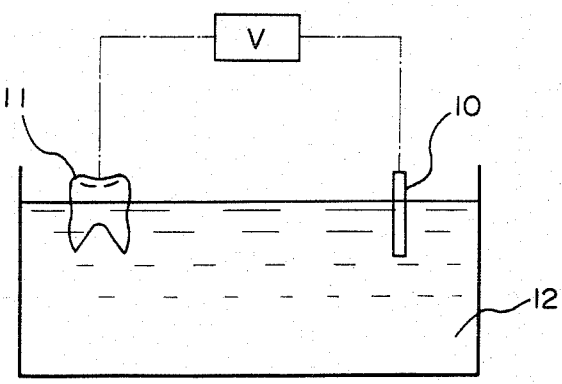
FIG. 7 schematically shows an experimental device.

In order to prove that a photovoltaic or photoelectromotive effect is present in use of the above devices, a simulation test was performed with an apparatus as schematically shown in FIG. 7. A $TiO_2$ stick 10 having a surface area of 1.2 $cm^2$ was immersed within a distilled water 12 together with a drawn decayed tooth 11 spaced apart from the stick. A receptacle containing the distilled water was placed in a room (when raining, at evening) and then the photovoltaic effect was measured. It was found that a photoelectromotive force of about 10 to 50 mV, which is sufficient for the aforementioned sanitary effect, was taking place under influence of the indoor natural light.

The main body 3 may be designed to have any shape other than the exemplified shapes without limiting the scope of the invention. The brush hairs 1a may be omitted from the main body, which may be provided with an attachment adapted to spray a teeth cleaning solution.

The semiconductors may be additionally activated by means of an external voltage so as to amplify the photoelectric effect, within the spirit of the invention. The $TiO_2$, which is optionally used in the device of the present invention, may be produced or prepared according to any one of the following methods instead of the method described: namely, (1) production and utilization of monocrystals;

(2) vacuum metallizing of a thin $TiO_2$ layer onto metallic Ti by means of the chemical vapor deposition (CVD) method or other methods;

(3) calcination of pelletized $TiO_2$ powders; and (4) production of a metallic Ti by means of anode oxidation.

It is reasonably assumed that the $TiO_2$ as the semiconductor 4 gives rise to the following reactions when irradiated with the light. Namely, $$TiO_2 + h\nu \rightarrow e^- + p^+,$$

$$H_2O + 2p \rightarrow \tfrac{1}{2}O_2 + 2H+ \text{ (on the } TiO_2\text{), and}$$

$$2H^+ + 2e^- \rightarrow H_2 \text{ (on the teeth).}$$

These reactions mean that the n-type semiconductor having the photoelectric effect will be activated by the light to release photoelectrons, which in turn build up an electron potential gradient between the semiconductor surface and an electrostatically charged environment surrounding the semiconductor surface, thereby producing a number of holes in the semiconductor. The teeth consequently become reverse-phased in their polarity due to a difference in electron density between them and the semiconductor. Thus, an oxidation reaction occurs in the vicinity of the semiconductor thereby releasing electrons from the saliva or water while the latter give electrons to the teeth thereby giving rise to a reduction reaction on the teeth.

Figure 8:
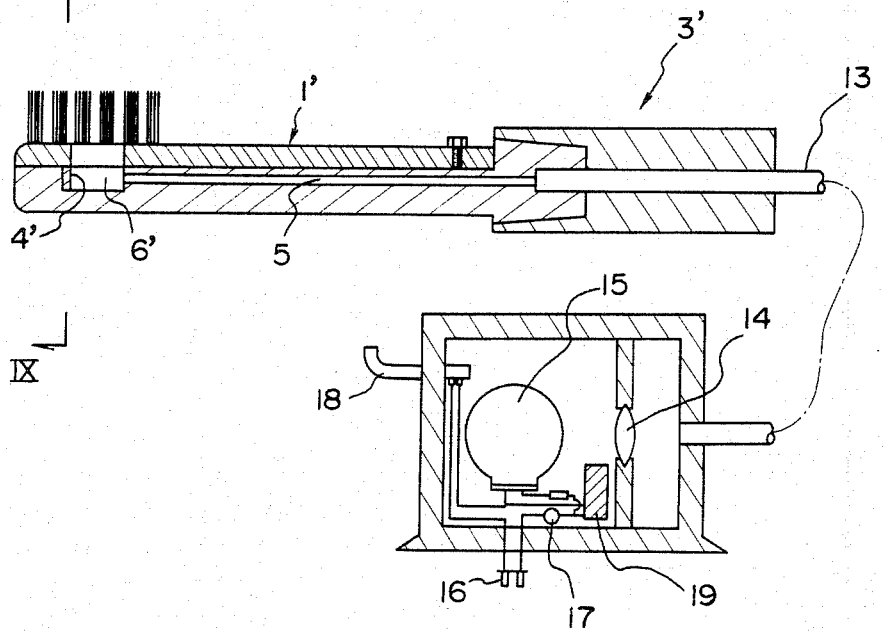
FIG. 8 is a vertical section of a further embodiment of the invention.
Figure 9:
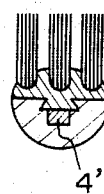
FIG. 9 is a cross section taken along the line IX—IX in FIG. 8.

FIGS. 8 and 9 illustrate another dental hygienic device in a modified embodiment.

An n-type semiconductor 4' having a photoelectric effect is disposed in a groove 6' formed in an inserting portion 1' of a main body 3'. Portion 1' is provided with a light conducting passage 5 that extends through the portion 1' to the groove 6' thereby irradiating the semiconductor with a man-made light supplied from one end of a glass fiber 13, the end being tightly connected with the passage end. The glass fiber 13 protrudes from the main body 3' and extends to a box provided with a lamp 15 adapted to illuminate the other end of the glass fiber 13 via a lens 14 opposed thereto. A power source plug 16, a main switch 17 for the lamp, and a hook-shaped switch 18 to be turned on and off in accordance with engagement and disengagement thereof with the main body 3' are operatively interconnected with lamp 15. A fan 19 is also provided for cooling the interior of the box heated by the lamp 15. It should be appreciated that the modified device in accordance with FIGS. 8 and 9 enables use of a semiconductor having a lower photosensitivity by virtue of the abovesaid strong irradiation which will force the semiconductor to give a sufficient photoelectric effect. In a case where a semiconductor having a good photosensitivity is used, its photoelectric effect will be greatly increased by use of the FIGS. 8 and 9 device.

We claim:

1. A dental hygienic device for the hygienic treatment of teeth in an oral cavity, said device comprising a main body having an insertion portion adapted to be brought into an operative position relative to water and/or saliva in the oral cavity, and semiconductor means consisting essentially of an n-type semiconductor material having a photoelectric effect, said semiconductor means including at least one portion disposed relative to said insertion portion so as to be simultaneously exposable to light and operatively communicable with the water and/or saliva of the oral cavity, said semiconductor means, in response to irradiation by light, for establishing at said one portion an electron density differential between said teeth and said semiconductor means to cause a reduction to occur at said teeth to thereby hygienically treat said teeth.

2. A device set forth in claim 1 wherein said semiconductor means includes an n-type semiconductor member exposed to light on said main body and and conductive wire means extending from said semiconductor member to the insertion portion.

3. A device as set forth in claim 1 further comprising brush means upstanding from the insertion portion for brushing the teeth.

4. A device as set forth in claim 3 wherein the semiconductor member is titanium dioxide manufactured by intensely heating elemental titanium at 1200° to 1500° C. in an incandescent state for 2 to 5 minutes.

5. A device as set forth in claim 1 further comprising light-irradiating means for irradiating the semiconductor means with a man-made light.

6. A device as set forth in claim 5 wherein said light-irradiating means includes lamp means to provide a source of light, lens means for focussing the light projected from the lamp means and glass fiber means operatively connecting said semiconductor means and said light-irradiating means for conducting the light provided by said lamp means and focused by said lens means to the semiconductor means.

7. A device as in claim 1 wherein said insertion portion includes means defining a groove to retain water and/or saliva therein, said groove for exposing said one portion of said semiconductor means to said water and/or saliva.

8. A device as in claim 1 wherein said main body includes means defining an opposing pair of grooves, said semiconductor means being disposed intermediate said pair of grooves so as to be exposable to light thereby.

9. A device as in claim 1 wherein said semiconductor material is in the form of a closed loop, at least one surface of said loop being disposed at an exterior region of said main body so as to be exposable to light.

10. A device as in claim 9 wherein said loop includes upper and lower surfaces each disposed at an exterior region of said main body so as to be exposable to light.

* * * * *